United States Patent
Kecskemethy et al.

(10) Patent No.: US 11,488,306 B2
(45) Date of Patent: Nov. 1, 2022

(54) IMMEDIATE WORKUP

(71) Applicant: Kheiron Medical Technologies Ltd, London (GB)

(72) Inventors: Peter Kecskemethy, London (GB); Tobias Rijken, London (GB); Edith Karpati, Budapest (HU); Michael O'Neill, London (GB); Andreas Heindl, London (GB); Joseph Elliot Yearsley, London (GB); Dimitrios Korkinof, London (GB); Galvin Khara, London (GB)

(73) Assignee: KHEIRON MEDICAL TECHNOLOGIES LTD, London (GB)

( * ) Notice: Subject to any disclaimer, the term of this patent is extended or adjusted under 35 U.S.C. 154(b) by 0 days.

(21) Appl. No.: 17/251,417

(22) PCT Filed: Jun. 14, 2019

(86) PCT No.: PCT/GB2019/051666
§ 371 (c)(1),
(2) Date: Dec. 11, 2020

(87) PCT Pub. No.: WO2019/239153
PCT Pub. Date: Dec. 19, 2019

(65) Prior Publication Data
US 2021/0312618 A1      Oct. 7, 2021

(30) Foreign Application Priority Data

Jun. 14, 2018 (GB) .................................... 1809796
Nov. 27, 2018 (GB) .................................... 1819329
Jan. 7, 2019   (GB) .................................... 1900212

(51) Int. Cl.
*G06T 7/00*      (2017.01)
*G06T 7/11*      (2017.01)
(Continued)

(52) U.S. Cl.
CPC ............ *G06T 7/0012* (2013.01); *A61B 6/502* (2013.01); *A61B 6/5205* (2013.01);
(Continued)

(58) Field of Classification Search
CPC ......... G06T 7/0012; G06T 7/11; G06T 7/143; G06T 7/70; G06T 2207/10081;
(Continued)

(56) References Cited

U.S. PATENT DOCUMENTS 5,768,406 A    6/1998   Abdel-Mottaleb
5,999,639 A   12/1999   Rogers et al.
(Continued)

FOREIGN PATENT DOCUMENTS

CN    105931226 A    9/2016
CN    106096491 A   11/2016
(Continued)

OTHER PUBLICATIONS

He et al., "A Review on Automatic Mammographic Density and Parenchymal Segmentation", International journal of breast cancer vol. 2015 (2015): 276217, pp. 1-31 (Year: 2015).*
(Continued)

*Primary Examiner* — Nay A Maung
*Assistant Examiner* — Jose M Torres
(74) *Attorney, Agent, or Firm* — Finch & Maloney PLLC

(57) ABSTRACT

The present invention relates to deep learning implementations for medical imaging. More particularly, the present invention relates to a method and system for indicating whether additional medical tests are required after analysing an initial medical screening, in substantially real-time. Aspects and/or embodiments seek to provide a method and system for recommending additional medical tests, in sub-
(Continued)

stantially real-time, based on analysing an initial medical scan, with the use of deep learning.

20 Claims, 4 Drawing Sheets

(51) Int. Cl.
G06T 7/70 (2017.01)
G16H 30/40 (2018.01)
A61B 6/00 (2006.01)
G06N 3/08 (2006.01)
G16H 30/20 (2018.01)
G16H 50/20 (2018.01)
G06T 7/143 (2017.01)
G16H 40/67 (2018.01)
G06V 10/764 (2022.01)
G06V 10/774 (2022.01)
G06V 30/19 (2022.01)
G06K 9/62 (2022.01)

(52) U.S. Cl.
CPC .......... A61B 6/5217 (2013.01); A61B 6/5235 (2013.01); G06K 9/6256 (2013.01); G06K 9/6267 (2013.01); G06N 3/08 (2013.01); G06T 7/11 (2017.01); G06T 7/143 (2017.01); G06T 7/70 (2017.01); G06V 10/764 (2022.01); G06V 10/774 (2022.01); G06V 30/19147 (2022.01); G06V 30/19173 (2022.01); G16H 30/20 (2018.01); G16H 30/40 (2018.01); G16H 40/67 (2018.01); G16H 50/20 (2018.01); G06T 2207/10081 (2013.01); G06T 2207/10088 (2013.01); G06T 2207/10116 (2013.01); G06T 2207/10132 (2013.01); G06T 2207/20076 (2013.01); G06T 2207/20081 (2013.01); G06T 2207/20084 (2013.01); G06T 2207/30068 (2013.01); G06T 2207/30096 (2013.01); G06V 2201/03 (2022.01)

(58) Field of Classification Search
CPC . G06T 2207/10088; G06T 2207/10116; G06T 2207/10132; G06T 2207/20076; G06T 2207/20081; G06T 2207/20084; G06T 2207/30068; G06T 2207/30096; A61B 6/502; A61B 6/5205; A61B 6/5217; A61B 6/5235; A61B 6/7267; A61B 6/025; A61B 6/032; A61B 6/54; A61B 6/467; A61B 8/0825; A61B 8/467; A61B 8/5223; A61B 5/7267; G06K 9/6256; G06K 9/6267; G06K 2209/05; G06N 3/08; G16H 30/20; G16H 30/40; G16H 40/67; G16H 50/20; G06V 10/764; G06V 10/774; G06V 30/19147; G06V 30/19173; G06V 2200/03; G06V 2201/03
See application file for complete search history.

(56) References Cited

U.S. PATENT DOCUMENTS

| 6,058,322 | A | 5/2000 | Nishikawa et al. |
| 6,075,879 | A | 6/2000 | Roehrig et al. |
| 6,463,425 | B2 | 10/2002 | Raz |
| 6,574,304 | B1 | 6/2003 | Hsieh |
| 7,490,085 | B2 | 2/2009 | Walker et al. |
| 9,589,374 | B1 | 3/2017 | Gao et al. |
| 10,223,610 | B1 | 3/2019 | Akselrod-Ballin et al. |
| 2004/0184644 | A1 | 9/2004 | Leichter et al. |
| 2004/0228509 | A1 | 11/2004 | Holupka et al. |
| 2005/0010445 | A1 | 1/2005 | Krishnan et al. |
| 2005/0049497 | A1 | 3/2005 | Krishnan |
| 2005/0113651 | A1 | 5/2005 | Wood et al. |
| 2006/0100507 | A1 | 5/2006 | Mertelmeier |
| 2006/0122467 | A1 | 6/2006 | Harrington et al. |
| 2006/0177125 | A1 | 8/2006 | Chan et al. |
| 2007/0003119 | A1 | 1/2007 | Roehrig et al. |
| 2007/0183641 | A1 | 8/2007 | Peters et al. |
| 2008/0159613 | A1 | 7/2008 | Luo et al. |
| 2009/0041327 | A1 | 2/2009 | Chen et al. |
| 2009/0118640 | A1* | 5/2009 | Miller .................... A61B 90/36 600/567 |
| 2009/0274349 | A1 | 11/2009 | Cascio et al. |
| 2010/0135562 | A1 | 6/2010 | Greenberg et al. |
| 2010/0256459 | A1 | 10/2010 | Miyasa et al. |
| 2010/0256991 | A1 | 10/2010 | Ishikawa et al. |
| 2011/0123087 | A1 | 5/2011 | Nie et al. |
| 2011/0150313 | A1 | 6/2011 | Su et al. |
| 2012/0099771 | A1* | 4/2012 | Lao .......................... G06T 7/42 382/131 |
| 2013/0218045 | A1 | 8/2013 | Ironstone |
| 2013/0236078 | A1 | 9/2013 | Kobayashi et al. |
| 2013/0322711 | A1 | 12/2013 | Schultz et al. |
| 2013/0343626 | A1 | 12/2013 | Rico et al. |
| 2014/0018681 | A1 | 1/2014 | Chang et al. |
| 2014/0355840 | A1 | 12/2014 | Pearson Peyton |
| 2016/0314579 | A1* | 10/2016 | Ghouti .................... G06V 10/42 |
| 2016/0350946 | A1 | 12/2016 | Schieke et al. |
| 2016/0361121 | A1 | 12/2016 | Reicher et al. |
| 2016/0364528 | A1 | 12/2016 | Reicher et al. |
| 2016/0364857 | A1 | 12/2016 | Reicher |
| 2017/0200266 | A1* | 7/2017 | Podilchuk ............ G06K 9/6278 |
| 2018/0033144 | A1 | 2/2018 | Risman et al. |
| 2018/0129900 | A1 | 5/2018 | Kiraly et al. |
| 2018/0165809 | A1 | 6/2018 | Stanitsas et al. |
| 2018/0218497 | A1 | 8/2018 | Golden et al. |
| 2019/0189263 | A1 | 6/2019 | Stoval, III et al. |
| 2019/0340763 | A1* | 11/2019 | Laserson .............. A61B 6/5235 |
| 2020/0074632 | A1 | 3/2020 | Heindl et al. |
| 2021/0035296 | A1* | 2/2021 | Mahrooghy ......... A61B 8/0825 |
| 2021/0248744 | A1 | 8/2021 | Rijken et al. |
| 2021/0313043 | A1 | 10/2021 | Kecskemethy et al. |

FOREIGN PATENT DOCUMENTS

| CN | 106204587 A | 12/2016 |
| GB | 2579244 A8 | 6/2020 |
| JP | 2008541889 A | 11/2008 |
| JP | 2013-039230 A | 2/2013 |
| WO | 9905503 | 2/1999 |
| WO | 2005001740 A2 | 1/2005 |
| WO | 2005001742 A3 | 1/2005 |
| WO | 2008050332 A2 | 5/2008 |
| WO | 2008088478 A1 | 7/2008 |
| WO | 2015031641 A1 | 3/2015 |
| WO | 2015077076 A1 | 5/2015 |
| WO | 2017210690 A1 | 12/2017 |
| WO | 2018189541 A1 | 10/2018 |
| WO | 2018189549 A1 | 10/2018 |
| WO | 2018189550 A1 | 10/2018 |
| WO | 2018189551 A1 | 10/2018 |

OTHER PUBLICATIONS

UK Intellectual Property Office; Search Report for GB1819329.2 dated May 28, 2019.
UK Intellectual Property Office; Search Report for GB1809796.4 dated Dec. 17, 2018.
WOSA, PCT/GB2019/051666.
IPRP, PCT/GB2019/051666, dated Oct. 7, 2020.
Canadian Intellectual Property Office; Examiner's Requisition for Application No. 3,102,173 (PCT No. GB2019051667) dated Jun. 29, 2021.
Canadian Intellectual Property Office; Examiner's Requisition for Application No. 3, 102, 174 (PCT No. GB2019051668) dated Jul. 6, 2021.
Intl Search Report, PCT/GB2019/051667, dated Nov. 1, 2019.

(56) References Cited

OTHER PUBLICATIONS

Intl Search Report, PCT/GB2019/051668, dated Nov. 6, 2019.
Intl Search Report, PCT/GB2019/051666, dated Sep. 23, 2019.
Canadian Patent Application 3,102,170, Requisition by Examiner dated Jul. 27, 2021.
K. He, G. Gkioxari, P. Dollár and R. Girshick, "Mask R-CNN," 2017 IEEE International Conference on Computer Vision (ICCV), 2017, pp. 2980-2988, doi: 10.1109/ICCV.2017.322.
Paul F. Jaeger et al "Retina U-Net: Embarrassingly Simple Exploitation of Segmentation Supervision for Medical Object Detection" (https://arxiv.org/pdf/1811.08661.pdf).
EP Patent Appln 19744778.2, "Communication Under Rule 71(3) EPC", Intention to Grant.
EP Patent Appln 19744779.0, "Communication Under Rule 71(3) EPC", Intention to Grant.
EP Patent Appln 19744777.4, "Communication Under Rule 71(3) EPC", Intention to Grant, dated Sep. 30, 2021.
Dezso Ribli et al. "Detecting and classifying lesions in mammograms with Deep Learning", Sci Rep 2018: 8: 4165, published online Mar. 15, 2018. Doi: 10.1038/s41598-018-22437-z.
Z Huo et al, "Computerized analysis of multiple-mammographic views: potential usefulness of special view mammograms in computer-aided diagnosis", IEEE Trans Med Imaging Dec. 2001; 20(12):1285-92, DOI: 10.1109/42.974923 (Abstract).
Yufeng Zheng et al. "Breast Cancer Screening Using Convolutional Neural Network and Follow-up Digital Mammography", Proceedings of spie, vol. 10669, May 14, 2018 (May 4, 2018), pp. 1066905-1066905, XP060105634, DOI: 10.1117/12.2304564.
Kisilev Pavel et al., "Medical Image Description Using Multi-task loss CNN", Sep. 27, 2016, Intelligent Virtual Agent.IVA 2015. LNCS: [Lecture Notes in Computer Science: Lect. Notes in Comuter], Springer, Berlin, Heidelberg, pp. 121-129, XP047410045, ISBN: 978-3-642-17318-9.
Written Opinion of the International Searching Authority, PCT/GB2019/051667.
IPRP, PCT/GB2019/051667, dated May 10, 2020.
Written Opinion of the International Searching Authority, PCT/GB2019/051668.
IPRP, PCT/GB2019/051668, dated May 10, 2020.
Written Opinion of the International Searching Authority, PCT/GB2019/051666.
IPRP, PCT/GB2019/051666, dated May 10, 2020.
International Search Report and Written Opinion received for Patent Application No. PCT/GB2018/050969, dated Jun. 26, 2018. 20 pages.
International Preliminary Report on Patentability received for Patent Application No. PCT/GB2018/050969, dated Oct. 15, 2019. 12 pages.
International Search Report and Written Opinion received for PCT Application No. PCT/GB2018/050980, dated Jul. 12, 2018. 34 pages.
International Preliminary Report on Patentability received for PCT Application No. PCT/GB2018/050980, dated Oct. 15, 2019. 11 pages.
Combined Search and Examination Report under Sections 17 and 18(3) received for GB Application No. 1711558.5, dated Dec. 22, 2017. 6 pages.
International Search Report and Written Opinion received for Patent Application No. PCT/GB2018/050979, dated Jul. 9, 2018. 36 pages.
International Preliminary Report on Patentability received for Patent Application No. PCT/GB2018/050979, dated Oct. 15, 2019. 11 pages.
Combined Search and Examination Report under Sections 17 and 18(3) received for GB Application No. 1711557.7, dated Jan. 18, 2018. 5 pages.
International Search Report and Written Opinion received for Patent Application No. PCT/GB2018/050981, dated Jul. 9, 2018. 23 pages.
International Preliminary Report on Patentability received for Patent Application No. PCT/GB2018/050981, dated Oct. 15, 2019. 15 pages.
Combined Search and Examination Report under Sections 17 and 18(3) received for GB Application No. 1711559.3 dated Dec. 19, 2017. 7 pages.
Christ, et al., "Automatic Liver and Tumor Segmentation of CT and MRI Volumes Using Cascaded Fully Convolutional Neural Networks," arXiv: 1702.05970v2 [cs.CV], Feb. 23, 2017. 20 pages.
Christ, et al., "Survivalnet: Predicting Patient Survival From Diffusion Weighted Magnetic Resonance Images Using Cascaded Fully Convolutional and 3D Convolutional Neural Networks," arXiv: 1702.05941v1 [cs.CV], Feb. 20, 2017. 6 pages.
Hou, et al., "Patch-based Convolutional Neural Network for Whole Slide Tissue Image Classification," IEEE Conference on Computer Vision and Pattern Recognition, (CVPR) Jun. 27, 2016. pp. 2424-2433.
Menechelli, et al., "Automatic breast tissue density estimation scheme in digital mammography images," Progress in Biomedical Optics and Imaging, SPIE—International Society for Optical Engineering., vol. 10136, Mar. 10, 2017. 12 pages.
Ronneberger, et al., "U-Net: Convolutional Networks for Biomedical Image Segmentation," Medical Image Computing and Computer-Assisted Intervention—MICCAI 2015—18th International Conference. Nov. 18, 2015, Springer International Publishing, arXiv:1505.04597v1, May 18, 2015. 8 pages.
Yu, et al., "Automated Melanoma Recognition in Dermoscopy Images via Very Deep Residual Networks," IEEE Transactions on Medical Imaging. Dec. 2016. 12 pages.
Canadian Office Action recieved for CN Application No. 3,102,170, dated Jan. 11, 2022. 5 pages.
El Hamdi, et al., "Breast Cancer Diagnosis Using a Hybrid Evolutionary Neural Network Classifier," 18th Mediterranean Conference on Control & Automation, Jun. 23-25, 2010, pp. 1308-1315.
Kallenberg, et al, "Unsupervised Deep Learning Applied to Breast Density Segmentation and Mammographic Risk Scoring," IEEE Transactions on Medical Imaging, vol. 35, No. 5, May 2016. pp. 1322-1331.
Winkel, et al., "Mammographic density and structural features can individually and jointly contribute to breast cancer risk assessment in mammography screening: a case-control study," BMC Cancer (2016) DOI 10.1186/s12885-016-2450-7. pp. 1-12.
Communication pursuant to Article 94(3) EPC received for EP Application No. 18719271.1, dated Jun. 21, 2021. 10 pages.
Communication pursuant to Article 94(3) EPC received for EP Application No. 18719272.9, dated Jun. 21, 2021. 8 pages.
Sun, et al., "Enhancing deep convolutional neural network scheme for breast cancer diagnosis with unlabeled data," Computerized Medical Imaging and Graphics, 57 (2017)4-9; retrieved at https://www.sciencedirect.com/science/article/am/pii/S0895611116300696.
Gram, et al, "The Tabar classification of mammographic parenchymal patterns," European Journal of Radiology 24 (1997) 131-136.
Akselrod-Ballin, et al., "A Region Based Convolutional Network for Tumor Detection and Classification in Breast Mammography," G. Carneiro et al. (Eds.): Labels 2016/DLMIA 2016, LNCS 10008, pp. 197-205.
U.S. Appl. No. 17/251,398, office action dated Sep. 1, 2021.
U.S. Appl. No. 17/251,354, office action dated Aug. 3, 2021.
JP Office Action received for JP Application No. 2020-505540, dated Apr. 19, 2022. 3 pages.
Canadian Intellectual Property Office; Examiner's Requisition for Application No. 3,102,173, (PCT No. GB20190516670 dated Dec. 9, 2021. 6 pages.

* cited by examiner

IMMEDIATE WORKUP

CROSS REFERENCE TO RELATED APPLICATIONS

This application is a national stage patent application filed under 35 U.S.C. § 371 of PCT International patent application PCT/GB2019/051666, filed Jun. 14, 2019, and claiming priority to GB patent application 1809796.4, filed Jun. 14, 2018, GB patent application 1819329.2, filed Nov. 27, 2018 and GB patent application 1900212.0 filed Jan. 7, 2019, the entire contents of each of which are incorporate by reference.

FIELD

The present invention relates to deep learning implementations for medical imaging. More particularly, the present invention relates to a method and system for indicating whether additional medical tests are required after preliminary analysis during an initial medical screening, in substantially real-time.

BACKGROUND

Mammography is an advanced method of scanning human breast tissue which makes use of low dose X-rays to produce images of the internal structure of the human breast. The screening of these images, called mammograms, aids early detection and diagnoses of breast abnormalities and diseases. In order to ascertain a more accurate scan, mammogram machines usually have two plates that compress the breast to spread the tissue apart and help radiologists examine the mammogram.

Assessment by human manpower, believed to be the most accurate method of image evaluation, refers to the task performed by a radiologist or similar professional, of inspecting medical scans, section by section, for a comprehensive analysis. However, considering a mammogram is a representation of three-dimensional information projected onto a two-dimensional image plane, there is often superimposition of tissues in the 2D medical scan images (mammograms) being inspected. As a result, tissues that appear superimposed within the image of the breast can reduce the visibility of malignant abnormalities or sometimes even simulate the appearance of an abnormality (false positive). This makes the task of analysing a mammogram more challenging and can cause difficulty when it comes to accurately and precisely detecting abnormalities.

Thus, the current methods of screening and requesting a workup (further medical tests including for example using alternative imaging techniques) can be inefficient and/or slow when relying on radiologist alone to examine unclear mammograms. Often, the end result is an unnecessary and costly recall procedure, biopsy and/or psychological stress for patients.

Additionally, if there is a suspicious finding in a mammogram and a further test is required, under the current medical screening regimes, the call back time for an additional test is usually two to three weeks.

SUMMARY OF INVENTION

Aspects and/or embodiments seek to provide a method and system for recommending or indicating the requirement for additional medical tests, in substantially real-time, based on analysing an initial medical scan, with the use of deep learning.

According to a first aspect, there is provided a computer-aided method of analysing medical images in substantially real-time, the method comprising the steps of: receiving one or more medical images; analysing said one or more medical images to determine one or more characteristics; and generating output data based on the determined one or more characteristics, wherein the output data is indicative of a requirement to obtain one or more additional medical tests.

Conventional methods for analysing medical images and making a decision to ascertain further medical tests rely on experts, usually a radiologist, to identify an abnormality in a mammogram. Often, there is a delay for the radiologist to examine the mammogram. Further radiologists do not demonstrate consistent accuracy due to the manual nature of the task, for example, making errors due to superimposed breast tissues in the mammogram and/or details too fine for the human eye to detect. Conversely, the method disclosed herein provides a way to analyse a medical image without any human input and provide an instantaneous recommendation as to whether a further medical test is required.

Optionally, the one or more additional medical tests comprise any or any combination of: a computerised tomography (CT) scan; an ultrasound scan; a magnetic resonance imaging (MRI) scan; a tomosynthesis scan; and/or a biopsy.

A further medical test can be suggested based on the analysis of the preliminary screening. As an example, a more detailed tomosynthesis scan can be instantaneously recommended if the initial mammogram is unclear or features are superimposed or there might be a lesion worth investigating. In some cases, the analysis from the initial medical image may not require any further workup or medical tests. Optionally, the output data may also indicate a breast density or tissue classification type.

Optionally, the one or more medical images comprises one or more mammographic or X-ray scans.

In most medical screening programmes, X-ray or mammography is the first type of medical scan.

Optionally, the step of analysing and determining is performed using one or more trained machine learning models.

Trained machine learning models can analyse medical images far quicker than a human expert, and hence increase the number of medical images analysed overall. The accuracy is typically consistent when using a machine learning model. Thus a problem, for example the growth of a cancerous tumour, can be detected more quickly than waiting for a human expert to become available and hence treatment may begin earlier or an additional medical test may be requested sooner. The identification of regions of interest, which may include lesions, may therefore aid screening and clinical assessment of breast cancer among other medical issues. Earlier diagnosis and treatment can reduce psychological stress to a patient and also increase the chances of survival in the long term.

Optionally, the trained machine learning models comprise convolutional neural networks.

Convolutional networks are powerful tools inspired by biological neural processes, which can be trained to yield hierarchies of features and are particularly suited to image recognition. Convolutional layers apply a convolutional operation to an input and pass the results to a following layer. With training, convolutional networks can achieve expert-level accuracy or greater with regard to segmenting and localising anatomical and pathological regions in digital medical images such as mammograms.

Optionally, the step of analysing and determining comprises segmenting one or more anatomical regions. Optionally, the output data further comprises overlay data indicating a segmentation outline and/or a probability masks showing one or more locations of one or more segmented regions.

Providing a clear and accurate segmentation of regions can be very helpful when reviewing a medical image, such as a mammogram. This may be especially relevant if there is reason to suspect there is a medical issue with a patient, for example a swollen area which is larger than it was in previous scans. Such changes may be more easily detectable if the different regions are clearly segmented. In addition, the segmentation information can also be used to enrich the Picture Archiving Communication Systems (PACS) that radiology departments use in hospitals. With the inclusion of this segmentation data on PACS, it advantageously improves future methods of flagging up similar cases, whether the methods are semi-automated, entirely automated or performed manually.

Optionally, the step of analysing and determining comprises identifying tissue type and density category. Optionally, the required type of the one or more additional medical tests are dependent upon the density category determined based on the one or more medical images. Optionally, this step may jointly estimate tissue type and density category.

Correctly classifying the tissue type and density category can enable the method to recommend an appropriate additional medical test or specific workup.

Optionally, the step of analysing and determining comprises automatically identifying one or more anomalous regions in the medical image.

Optionally, the step of analysing and determining comprises identifying and distinguishing between a malignant lesion and/or a benign lesion and/or typical lesion.

Optionally, the output data further comprises overlay data indicating a probability mask for the one or more lesions.

Optionally, the step of analysing and determining comprises identifying architectural distortion.

Optionally, the one or more medical images and the one or more additional medical images comprise the use digital imaging and communications in medicine, DICOM, files.

As a DICOM file is conventionally used to store and share medical images, conforming to such a standard can allow for easier distribution and future analysis of the medical images and/or any overlays or other contributory data. The one or more binary masks may be stored as part of a DICOM image file, added to an image file, and/or otherwise stored and/or represented according to the DICOM standard or portion of the standard.

According to a further aspect, there is provided a system for analysing medical images in substantially real-time, the system comprising: a medical imaging device 101; a picture archiving communication system (PACS 102); a processing unit 201 operable to analyse one or more medical images on the PACS 102 to determine one or more characteristics; and an output viewer 202 operable to display output data generated based on the determined one or more characteristics, wherein the output data is indicative of a requirement to obtain one or more additional medical images.

Such a system may be installed in or near hospitals, or connected to hospitals via a digital network, to reduce waiting times for medical images to be analysed. Patients may therefore be spared stress from not knowing the results of a medical scan and receive a decision more quickly.

Optionally, the processing unit 201 is integrated with the medical imaging device 101.

In this way, the medical scanner can be coupled with a processing unit 201 to analyse medical images as soon as they are scanned.

Optionally, the processing unit 201 is located remotely and is accessible via a communications channel.

In this configuration, the processing unit 201 can be deployed from a remote cloud system without need to replace and change existing scanning equipment.

According to a further aspect, there is provided a system operable to perform the method according to any other aspect.

According to a further aspect, there is provided a computer program operable to perform the method according to any other aspect.

Through the use of a computer or other digital technology, examination of medical images may be performed with greater accuracy, speed, and/or reliability that relying on a human expert. Therefore, a greater number of medical images may be reviewed at one time thereby reducing backlogs for experts and further reducing errors made when the medical images themselves are actually reviewed.

BRIEF DESCRIPTION OF DRAWINGS

Embodiments will now be described, by way of example only and with reference to the accompanying drawings having like-reference numerals, in which.

SPECIFIC DESCRIPTION

Referring to FIGS. 1 to 4, an embodiment will now be described.

Figure 1:
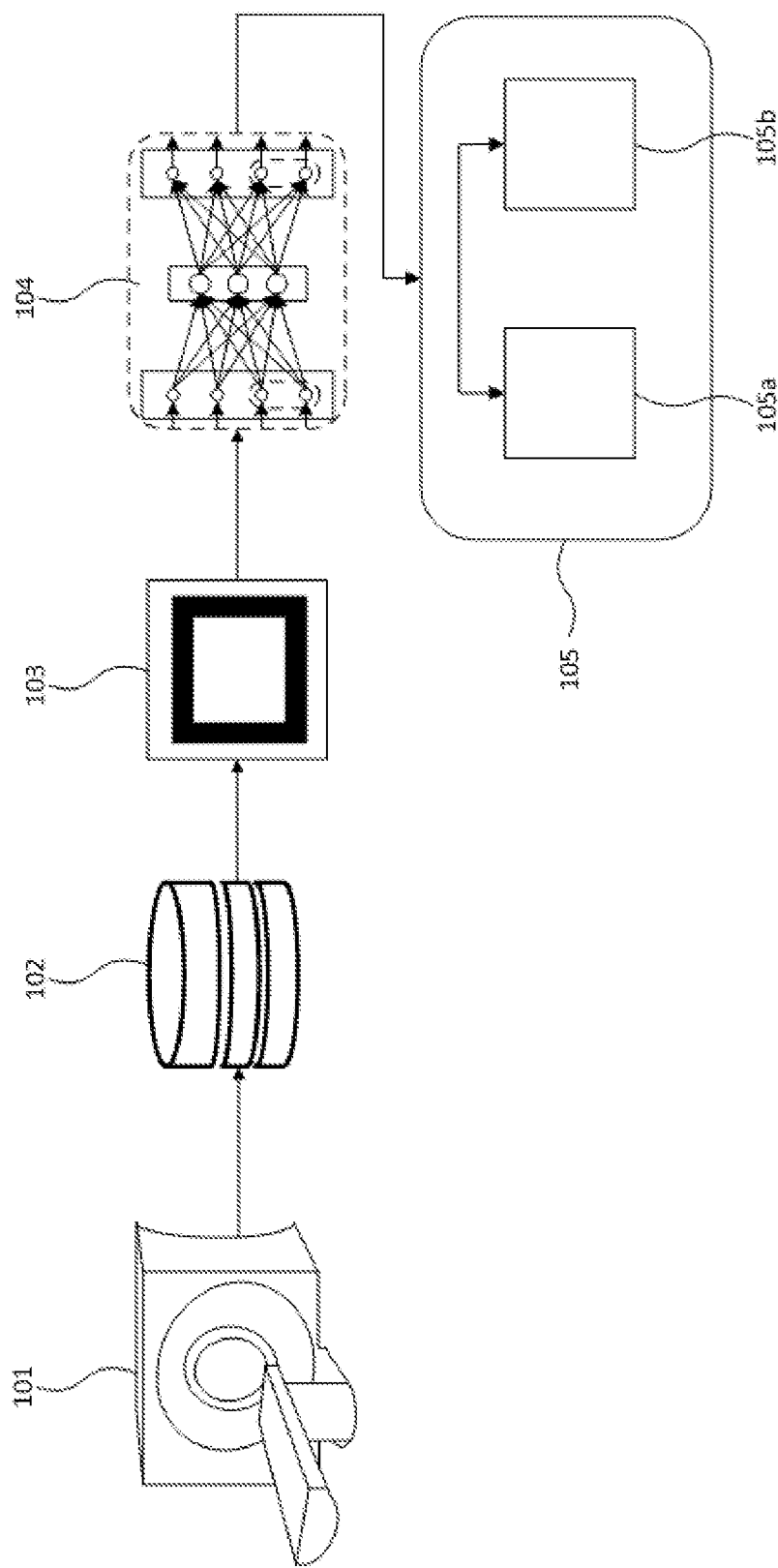
FIG. 1 shows a flow diagram of an embodiment.
Figure 2:
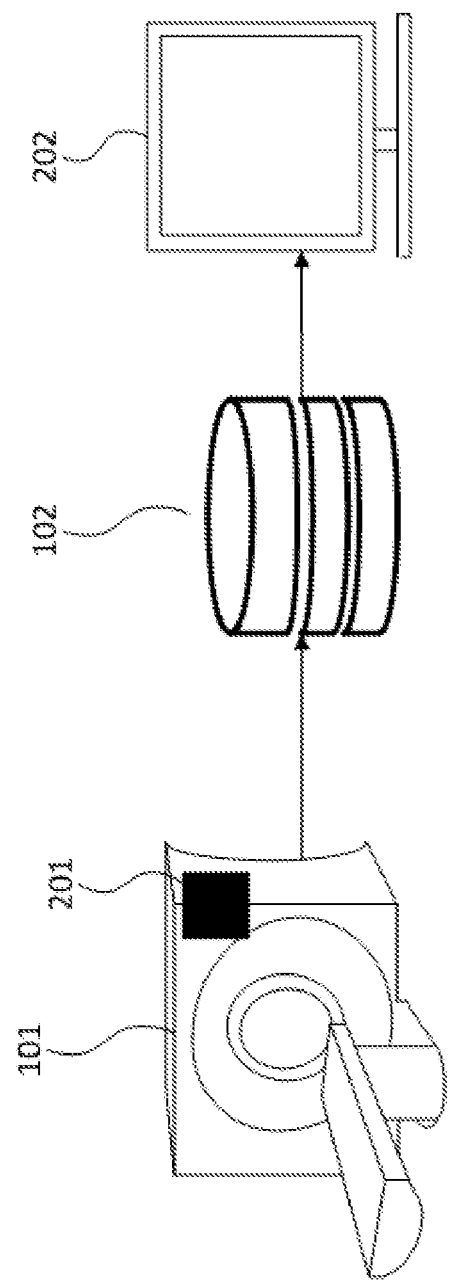
FIG. 2 depicts a first deployment (for example, within a medical scanning device)
Figure 3:
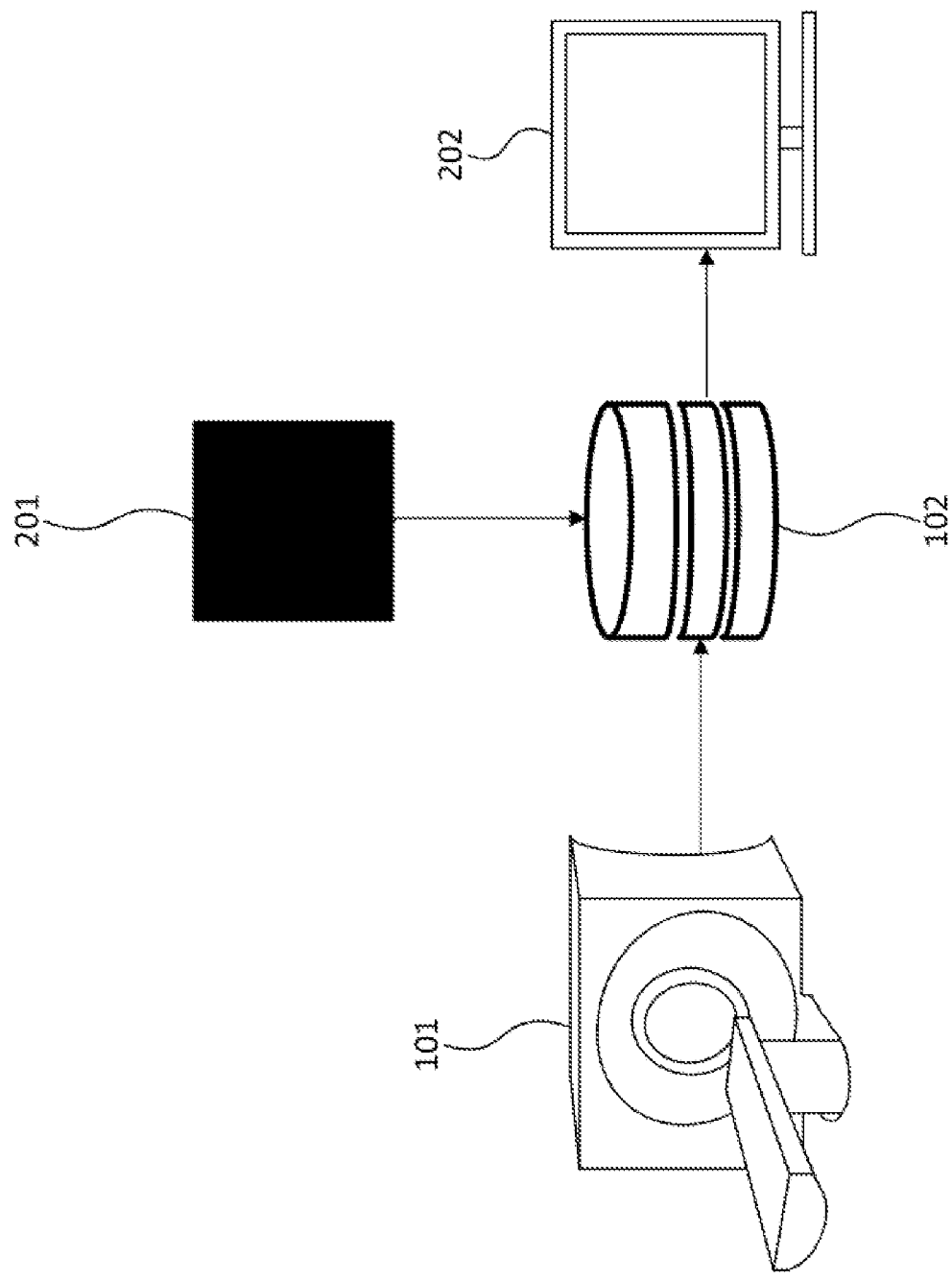
FIG. 3 depicts a second deployment (for example, on the premises of a medical facility)
Figure 4:
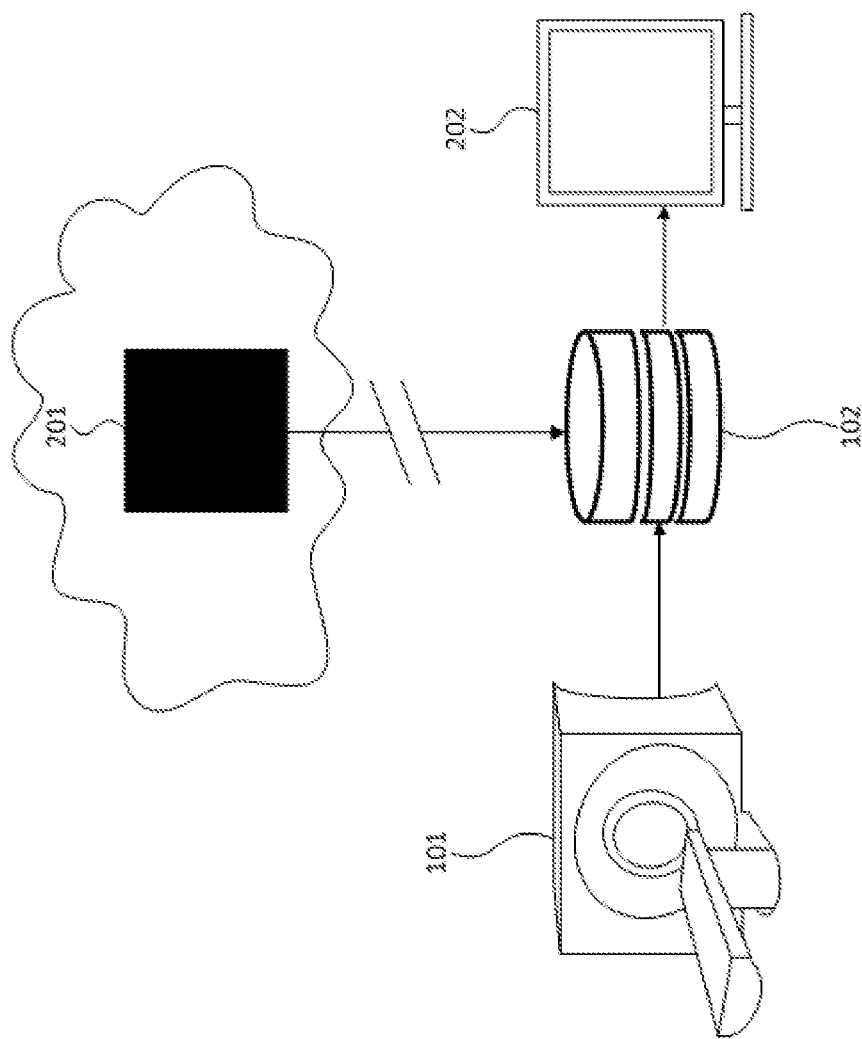
FIG. 4 depicts a third deployment (for example, using a cloud system).

As seen in FIG. 1, having performed a medical scan of a patient (such as a mammography) using a medical imaging scanner 101, the scanned images are collated in DICOM format, which is a file format commonly used to store medical images. The method uses pre-processed data that is stored on a Picture Archiving Communication Systems (PACS) 102 that radiology departments use in hospitals. The output of this method also enriches the PACS database to improve future applications of analysing mammographic images. Image data is extracted from the DICOM file and an image is generated.

The image then undergoes a pre-processing stage 103. The image is loaded onto a 4D tensor of size [1, width, height, 1]. The pre-processing stage may comprise windowing the image data to a predetermined windowing level. The windowing level defines the range of bit values considered in the image. Medical images are conventionally 16-bit images, wherein each pixel is represented as a 16-bit integer ranging from 0 to $2^{16}-1$, i.e. [0, 1, 2, . . . , 65535]. The information content is very high in these images, and generally comprises more information than what the human eye is capable of detecting. A set value for the windowing level is typically included within the DICOM file.

In some cases, it can be important to maintain image resolution. Often, conventional graphics processing unit (GPU) constraints require that the image is divided into a plurality of patches in order to maintain resolution. Each patch can then be provided to a Fully Convolutional Network (FCN). The larger the patch, the more context that can be provided but some precision may be lost. For example, in the case of a large image comprising a small tumour, if the FCN is instructed that somewhere in this patch there is a tumour, the network would need to learn how to find it first before it can be classified. In this embodiment patch sizes of 300×300 pixels are used, although larger and smaller patch sizes may be used.

A rescaling step may be included owing to above mentioned constraints of conventional hardware. Medical images are typically in the region of ~3500×2500 pixels. An FCN applied to this image does not fit in conventional graphics processing unit (GPU) memory. The image can be rescaled to a larger or smaller size, or even not rescaled at all, and would allow the FCN to see a higher resolution and may pick up finer detail. However, this is unlikely to fit in GPU memory, and could cause the method to become considerably slower. By rescaling the image to a smaller size, it is more likely to be able to fit in a GPU memory, and allow the processes to run at a faster speed. The FCN may also generalise better owing to a smaller number of input parameters.

The method may be used to identify and detect lesions in the mammograms. The lesions which may be segmented may comprise one or more cancerous growths, masses, abscesses, lacerations, calcifications, and/or other irregularities within biological tissue.

The images are analysed by feeding them through a trained machine learning model 104, such as a Convolutional Neural Network. This embodiment utilises deep learning techniques to train and develop the convolution network. The model is trained on a dataset with known workups and, hence, directly establishes a relationship between the images received and the known workups to estimate a required workup. In particular, the output 105 of the machine learning model 104 is a binary vector, where the indices represent various types of workup. For example, the workups may be any, or any combination of need no further action, an Ultrasound scan, a Tomosynthesis scan, an MRI scan and/or taking a Biopsy.

The dataset used for training the neural networks may also contain known density or tissue types. In that case, a multi-task learning approach can be taken to have the model also output density (A, B, C, D) or tissue type (1, 2, 3, 4, 5).

There are different types of patterns in breast tissue that affect the detectability of breast cancers. Thus, it is important to know what kind of pattern is present. There are five mammography parenchymal patterns known as "Tabar patterns", named after professor Laszlo Tabar who developed this classification.

The Tabar patterns (or classifications types) are based on a histologic-mammographic correlation with a three-dimensional, subgross (thick-slice) technique, and on the relative proportion of four "building blocks" (nodular densities, linear densities, homogeneous fibrous tissue, radiolucent fat tissue). The five classifications are as follows:
1. Balanced proportion of all components of breast tissue with a slight predominance of fibrous tissue
2. Predominance of fat tissue
3. Predominance of fat tissue with retroareolar residual fibrous tissue
4. Predominantly nodular densities
5. Predominantly fibrous tissue (dense breast)

Classes 4 and 5 are considered high risk, meaning that it is difficult to detect cancers in the breast with those patterns, whereas classes 1, 2 and 3 are considered lower risk as it is easier to spot cancerous regions.

Some therapies may alter the pattern by increasing parenchymal density, as in hormone replacement therapy (HRT), or reducing it as in therapies with selective oestrogen-receptor modulators (SERM).

Similarly, breast density categories are classified by radiologists using the BI-RADS system. Again, this classification is used for quality control purposes. For example, it is very difficult to spot an anomaly in dense breasts. There are four categories in the BI-RADS system:
A. The breasts are almost entirely fatty
B. There are scattered areas of fibroglandular density
C. The breasts are heterogeneously dense, which may obscure small masses
D. The breasts are extremely dense, which lowers the sensitivity of mammography Importantly, breast densities and tissue patterns are also known to have a mutual correlation to breast cancer development.

In some cases, the method can produce two types of output data. Whilst output data can relate to a suggested workup or additional medical tests 105a, the output data may also indicate the density or tissue classification 105b. The output data can indicate a binary output as to the requirement for further tests. Optionally, the output data can include data relating to how the binary output was reached, including any of; Tabar pattern; tissue classification types; breast density; nodular densities; linear densities; homogenous fibrous tissue; radiolucent fat tissue; BI-RADS category; a measure of superimposed features within the images; probability and/or confidence rating.

Mammography is a medical imaging modality widely used for breast cancer detection. Mammography makes use of "soft" X-rays to produce detailed images of the internal structure of the human breast—these images are called mammograms and this method is considered to be the gold standard in early detection of breast abnormalities which provide a valid diagnosis of a cancer in a curable phase.

Unfortunately, the procedure of analysing mammograms is often challenging. The density and tissue type of the breasts are highly varied and in turn present a high variety of visual features due to patient genetics. These background visual patterns can obscure the often tiny signs of malignancies which may then be easily overlooked by the human eye. Thus, the analyses of mammograms often lead to false-positive or false-negative diagnostic results which may cause missed treatment (in the case of false negatives) as well as unwanted psychological and sub-optimal downstream diagnostic and treatment consequences (in the case of false positives).

Most developed countries maintain a population-wide screening program, comprising a comprehensive system for calling in women of a certain age group (even if free of symptoms) to have regular breast screening. These screening programs require highly standardized protocols to be followed by experienced specialist trained doctors who can reliably analyse a large number of mammograms routinely. Most professional guidelines strongly suggest reading of each mammogram by two equally expert radiologists (also referred to as double-reading). Nowadays, when the number of available radiologists is insufficient and decreasing, the double-reading requirement is often impractical or impossible.

When analysing mammograms, the reliable identification of anatomical structures is important for visual evaluation and especially for analytic assessment of visual features based on their anatomic location and their relation to anatomic structures, which may have profound implications on the final diagnostic results. In the case that anatomic structures appear distorted they may also indicate the presence of possible malignancies.

Conventional X-ray is a medical imaging modality widely used for the detection of structural abnormalities related to the air containing structures and bones, as well as those diseases which have an impact on them. Conventional X-ray is the most widely used imaging method and makes use of "hard" X-rays to produce detailed images of the internal structure of the lungs and the skeleton. These images are called roentgenograms or simply X-rays.

Unfortunately, the procedure of analysing X-rays is often challenging, especially when analysing lung X-rays in order to detect infectious disease (e.g. TB) or lung cancer in early stage.

Cross-sectional medical imaging modalities are widely used for detection of structural or functional abnormalities and diseases which have a visually identifiable structural impact on the human internal organs. Generally, the images demonstrate the internal structures in multiple cross-sections of the body. The essence of the most widely used cross-sectional techniques are described below.

Computed tomography (CT) is a widely used imaging method and makes use of "hard" X-rays produced and detected by a specially rotating instrument and the resulted attenuation data (also referred to as raw data) are presented by a computed analytic software producing detailed images of the internal structure of the internal organs. The produced sets of images are called CT-scans which may constitute multiple series with different settings and different contrast agent phases to present the internal anatomical structures in cross sections perpendicular to the axis of the human body (or synthesized sections in other angles).

Magnetic Resonance Imaging (MRI) is an advanced diagnostic technique which makes use of the effect magnetic field impacts on movements of protons which are the utmost tiniest essential elements of every living tissue. In MRI machines the detectors are antennas and the signals are analysed by a computer creating detailed images if the internal structures in any section of the human body. MRI can add useful functional information based on signal intensity of generated by the moving protons.

However, the procedure of analysing any kind of cross-sectional images is often challenging, especially in the case of oncologic disease as the initial signs are often hidden and appearance of the affected areas are only minimally differed from the normal.

When analysing cross sectional scans, diagnosis is based on visual evaluation of anatomical structures. The reliable assessment, especially for analytic assessment, of visual appearance based on their anatomic location and their relation to anatomic structures, may have profound implications on final diagnostic results. In the case that anatomic structures appear distorted they may also indicate the presence of possible malignancies.

Generally, in the case of all diagnostic radiology methods (which include mammography, conventional X-ray, CT, MRI), the identification, localisation (registration), segmentation and classification of abnormalities and/or findings are important interlinked steps in the diagnostic workflow.

In the case of ordinary diagnostic workflows carried out by human radiologists, these steps may only be partially or sub-consciously performed but in the case of computer-based or computer-aided diagnoses and analyses the steps often need to be performed in a clear, concrete, descriptive and accurate manner.

Locality and classification may define and significantly influence diagnoses. Both locality and classification may be informed by segmentation in terms of the exact shape and extent of visual features (i.e. size and location of boundaries, distance from and relation to other features and/or anatomy). Segmentation may also provide important information regarding the change in status of disease (e.g. progression or recession).

Machine learning is the field of study where a computer or computers learn to perform classes of tasks using the feedback generated from the experience or data gathered that the machine learning process acquires during computer performance of those tasks.

Typically, machine learning can be broadly classed as supervised and unsupervised approaches, although there are particular approaches such as reinforcement learning and semi-supervised learning which have special rules, techniques and/or approaches. Supervised machine learning is concerned with a computer learning one or more rules or functions to map between example inputs and desired outputs as predetermined by an operator or programmer, usually where a data set containing the inputs is labelled.

Unsupervised learning is concerned with determining a structure for input data, for example when performing pattern recognition, and typically uses unlabelled data sets. Reinforcement learning is concerned with enabling a computer or computers to interact with a dynamic environment, for example when playing a game or driving a vehicle.

Various hybrids of these categories are possible, such as "semi-supervised" machine learning where a training data set has only been partially labelled. For unsupervised machine learning, there is a range of possible applications such as, for example, the application of computer vision techniques to image processing or video enhancement. Unsupervised machine learning is typically applied to solve problems where an unknown data structure might be present in the data. As the data is unlabelled, the machine learning process is required to operate to identify implicit relationships between the data for example by deriving a clustering metric based on internally derived information. For example, an unsupervised learning technique can be used to reduce the dimensionality of a data set and attempt to identify and model relationships between clusters in the data set, and can for example generate measures of cluster membership or identify hubs or nodes in or between clusters (for example using a technique referred to as weighted correlation network analysis, which can be applied to high-dimensional data sets, or using k-means clustering to cluster data by a measure of the Euclidean distance between each datum).

Semi-supervised learning is typically applied to solve problems where there is a partially labelled data set, for example where only a subset of the data is labelled. Semi-supervised machine learning makes use of externally provided labels and objective functions as well as any implicit data relationships. When initially configuring a machine learning system, particularly when using a supervised machine learning approach, the machine learning algorithm can be provided with some training data or a set of training examples, in which each example is typically a pair of an input signal/vector and a desired output value, label (or classification) or signal. The machine learning algorithm analyses the training data and produces a generalised function that can be used with unseen data sets to produce desired output values or signals for the unseen input vectors/signals. The user needs to decide what type of data is to be used as the training data, and to prepare a representative real-world set of data. The user must however take care to ensure that the training data contains enough information to accurately predict desired output values without providing too many features (which can result in too many dimensions being considered by the machine learning process during training and could also mean that the machine learning process does not converge to good solutions for all or specific examples). The user must also determine the desired structure of the learned or generalised function, for example whether to use support vector machines or decision trees.

The use of unsupervised or semi-supervised machine learning approaches are sometimes used when labelled data is not readily available, or where the system generates new labelled data from unknown data given some initial seed labels.

Machine learning may be performed through the use of one or more of: a non-linear hierarchical algorithm; neural network; convolutional neural network; recurrent neural network; long short-term memory network; multi-dimensional convolutional network; a memory network; fully convolutional network or a gated recurrent network allows a flexible approach when generating the predicted block of visual data. The use of an algorithm with a memory unit such as a long short-term memory network (LSTM), a memory network or a gated recurrent network can keep the state of the predicted blocks from motion compensation processes performed on the same original input frame. The use of these networks can improve computational efficiency and also improve temporal consistency in the motion compensation process across a number of frames, as the algorithm maintains some sort of state or memory of the changes in motion. This can additionally result in a reduction of error rates.

Developing a machine learning system typically consists of two stages: (1) training and (2) production. During the training the parameters of the machine learning model are iteratively changed to optimise a particular learning objective, known as the objective function or the loss. Once the model is trained, it can be used in production, where the model takes in an input and produces an output using the trained parameters.

During training stage of neural networks, verified inputs are provided, and hence it is possible to compare the neural network's calculated output to then the correct the network is need be. An error term or loss function for each node in neural network can be established, and the weights adjusted, so that future outputs are closer to an expected result. Backpropagation techniques can also be used in the training schedule for the or each neural network.

The model can be trained using backpropagation and forward pass through the network. The loss function for dense training is the sum over spatial dimensions of the loss functions of the individual pixels.

$$L(x) = \Sigma_{i,j} l'(x_{i,j})$$

here L(x) is the loss over the whole image and $l'(x_{i,j})$ is the loss for the pixel at i,j. This enables the system to automatically identify one or more lesions from the image created by the system.

The loss function may be the DICE loss, which is defined as $$L_{DSC} = \frac{2\sum_i^N s_i r_i}{\sum_i^N s_i + \sum_i^N r_i}$$

where $s_i$ and $r_i$ represent the continuous values of the prediction map $\in [0, \ldots, 1]$ and the ground truth at each pixel i, respectively. Alternatively, a cross-entropy can be used. The cross-entropy loss for the pixel at i, j is defined as $$L_{CE} = -\sum_{c=1}^{C} y * \log(s)$$

where C is the number of classes, $y \in \{0,1\}$ is the binary indicator for class c, and s is the score for class c. The loss for the full image, x, is defined as the sum over all the losses for the pixels:

$$L_{CE}(x) = \sum_{i,j}\left(-\sum_{c=1}^{C} y * \log(s)\right)$$

Once an output is generated by the neural network, one or more patches from the output may be sampled. The sampling may be proportional to the probability of the presence of lesions, in particular the sampling may be taken from areas with a higher probability of being a lesion as defined by a predetermined threshold. Alternatively, Poisson sampling or uniform sampling may be used to sample patches. Poisson sampling may give a better coverage of all of the breast tissue. The CNN may also be trained using the results of a different process, for example a Random Forest based candidate selector or any similar lesion detection method.

In the multitask learning setting, the loss will consist of multiple parts. A loss term for each task.

$$L(x) = \lambda_1 L_1 + \lambda_2 L_2$$

Where $L_1$, $L_2$ are the loss terms for two different tasks and $\lambda_1$, $\lambda_2$ are weighting terms.

Any system features as described herein may also be provided as method features, and vice versa. As used herein, means plus function features may be expressed alternatively in terms of their corresponding structure.

Any feature in one aspect may be applied to other aspects, in any appropriate combination. In particular, method aspects may be applied to system aspects, and vice versa. Furthermore, any, some and/or all features in one aspect can be applied to any, some and/or all features in any other aspect, in any appropriate combination.

It should also be appreciated that particular combinations of the various features described and defined in any aspects of the invention can be implemented and/or supplied and/or used independently.

The invention claimed is:

1. A computer-aided method of analysing medical images, the method comprising:
    receiving one or more medical images;
    analysing said one or more medical images to determine characteristics using one or more trained machine learning models, wherein the characteristics include at least a tissue type and a density category; and generating output data based on the determined characteristics, wherein the output data is indicative of a requirement to obtain one or more additional medical tests, further wherein the output data is based on at least the determined tissue type and density category.

2. The method of claim 1 wherein the one or more additional medical tests comprises any or any combination of: a computerised tomography (CT) scan; an ultrasound scan; a magnetic resonance imaging (MRI) scan; a tomosynthesis scan; and/or a biopsy.

3. The method of claim 2 wherein the one or more additional medical tests are dependent upon the density category determined based on the one or more medical images.

4. The method of claim 1 wherein the one or more medical images comprises one or more mammographic or X-ray scans.

5. The method of claim 1 wherein the one or more trained machine learning models comprise convolutional neural networks.

6. The method of claim 1 wherein the step of analysing comprises segmenting one or more anatomical regions.

7. The method of claim 6 wherein the output data further comprises overlay data indicating a segmentation outline and/or probability masks showing one or more locations of one or more segmented regions.

8. The method of claim 1 wherein the step of analysing comprises automatically identifying one or more anomalous regions in the one or more medical images.

9. The method of claim 1 wherein the step of analysing comprises identifying and distinguishing between a malignant lesion and/or a benign lesion and/or typical lesion.

10. The method of claim 9 wherein the output data further comprises overlay data indicating a probability mask for the one or more lesions.

11. The method of claim 1 wherein the step of analysing comprises identifying architectural distortion.

12. The method of claim 1 wherein the one or more medical images comprise digital imaging and communications in medicine, (DICOM), files.

13. A system for analysing medical images, the system comprising:
a medical imaging device;
a picture archiving communication system (PACS); and
a processing unit configured to
analyse the one or more medical images on the PACS to identify at least a tissue type and a density category using one or more trained machine learning models, and
generate output data based on at least the identified tissue type and density category, wherein the output data is indicative of a requirement to obtain one or more additional medical tests.

14. The system of claim 13 further comprising: an output viewer operable to display the output data.

15. The system of claim 13 wherein the processing unit is integrated with the medical imaging device.

16. The system of claim 13 wherein the processing unit is located remotely and is accessible via a communications channel.

17. The system of claim 16 wherein the processing unit is part of a computer system located within a remote cloud system.

18. The system of claim 13 wherein the medical imaging device includes x-ray equipment, mammography scanning equipment, or magnetic resonance imaging equipment.

19. The system of claim 13 wherein the one or more trained machine learning models comprise convolutional neural networks.

20. A non-transitory computer program product comprising instructions which, when the program is executed by a computer, cause the computer to carry out the method according to claim 1.

* * * * *